(12) United States Patent
Shamilov et al.

(10) Patent No.: US 12,156,701 B2
(45) Date of Patent: Dec. 3, 2024

(54) FORECASTED ELECTROANATOMICAL MAPS FOR ABLATION PLANNING

(71) Applicant: BIOSENSE WEBSTER (ISRAEL) LTD., Yokneam (IL)

(72) Inventors: Elias Shamilov, Eshhar (IL); Vladimir Rubinstein, Haifa (IL); Avram Dan Montag, Haifa (IL); Konstantin Feldman, Haifa (IL); Alexander Gorovoy, Kiryat Motzkin (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 600 days.

(21) Appl. No.: 17/498,384

(22) Filed: Oct. 11, 2021

(65) Prior Publication Data

US 2023/0109856 A1    Apr. 13, 2023

(51) Int. Cl.
| | | |
|---|---|---|
| A61B 5/316 | (2021.01) | |
| A61B 5/367 | (2021.01) | |
| A61B 18/14 | (2006.01) | |
| A61B 34/10 | (2016.01) | |
| A61B 18/00 | (2006.01) | |

(52) U.S. Cl.
CPC .............. *A61B 34/10* (2016.02); *A61B 5/367* (2021.01); *A61B 18/14* (2013.01); *A61B 2018/00351* (2013.01); *A61B 2018/00577* (2013.01); *A61B 2034/104* (2016.02); *A61B 2034/105* (2016.02)

(58) Field of Classification Search
CPC ........... A61B 2018/00577; A61B 2018/00839; A61B 5/339; A61B 2018/00351; A61B 5/316; A61B 2018/00642; A61B 2034/105; A61B 5/318; A61B 5/4836; A61B 34/10; A61B 2034/107; A61B 5/0036; A61B 6/503; A61B 5/7264; A61B 5/742; A61B 2017/00053; A61B 5/24; A61B 5/7235; A61B 5/05; A61B 5/00; A61B 5/6867; A61B 5/0004; A61N 1/3627; A61N 1/05; A61N 1/368
See application file for complete search history.

(56) References Cited

U.S. PATENT DOCUMENTS

| | | | |
|---|---|---|---|
| 5,391,199 A | 2/1995 | Ben | |
| 5,443,489 A | 8/1995 | Ben | |

(Continued)

OTHER PUBLICATIONS

European Search Report for corresponding EPA No. 22200488.9 dated Mar. 20, 2023.

(Continued)

*Primary Examiner* — Deborah L Malamud (57) ABSTRACT

A system includes a display and a processor. The processor is configured to compute multiple forecasted local activation times (LATs) at different respective locations on cardiac tissue of a subject, by simulating a propagation of a physiological activation potential along the cardiac tissue with a particular portion of the cardiac tissue, which is currently conductive, being non-conductive. The processor is further configured to generate, based on the forecasted LATs, a forecasted electroanatomical map representing a forecasted state of the cardiac tissue following an ablation of the particular portion of the cardiac tissue, and to display the forecasted electroanatomical map on the display. Other embodiments are also described.

16 Claims, 4 Drawing Sheets

(56) References Cited

U.S. PATENT DOCUMENTS

| | | | |
|---|---|---|---|
| 5,558,091 | A | 9/1996 | Acker |
| 5,944,022 | A | 8/1999 | Nardella |
| 5,983,126 | A | 11/1999 | Wittkampf |
| 6,177,792 | B1 | 1/2001 | Govari |
| 6,690,963 | B2 | 2/2004 | Ben |
| 6,788,967 | B2 | 9/2004 | Ben |
| 7,536,218 | B2 | 5/2009 | Govari |
| 8,456,182 | B2 | 6/2013 | Bar-Tal |
| 9,463,072 | B2 | 10/2016 | Comaniciu |
| 10,354,758 | B2 * | 7/2019 | Yang .............. G16H 50/50 |
| 2016/0058520 | A1 | 3/2016 | Yang |
| 2017/0027649 | A1 | 2/2017 | Kiraly |
| 2020/0114176 | A1 | 4/2020 | Phillips |
| 2020/0146579 | A1 | 5/2020 | Bar-Tal |
| 2020/0352652 | A1 | 11/2020 | Amit |

OTHER PUBLICATIONS

Alberola Garcia et al., "A Probabilistic Model of Cardiac Electrical Activity Based on a Cellular Automata System", Rev EspCardiel, vol. 58, No. 1, Jan. 1, 2005 (Jan. 1, 2005), pp. 41-47.

Nenonen J et al., "Computer model of propagated excitation in the anisotropic human heart. I. Implementation and algorithms", Proceedings of the Computers in Cardiology Meeting. Venice, Sep. 23-26, 1991; [Proceedings of the Computers in Cardiology Meeting], New York, IEEE, US, vol. MEETING 18, Sep. 23, 1991 (Sep. 23, 1991), pp. 545-548.

Evseev, Alexey A., "Cellular automata simulation on surface triangulation for diffusion processes", Bulletin of the Novosibirsk Computing Center, Series: Computer Science, vol. 30, 2010, pp. 1-13.

Dossel O et al., "A framework for personalization of computational models of the human atria", Engineering in Medicine and Biology Society,Embc, 2011 Annual International Conference of the IEEE, IEEE, Aug. 30, 2011 (Aug. 30, 2011), pp. 4324-4328.

Francisco Sahli Costabal, "Physics-Informed Neural Networks for Cardiac Activation Mapping", Original Research, Feb. 28, 2020, vol. 8, Article 42, pp. 1-12.

A.A. Evseev, "Cellular automata simulation on surface triangulation for diffusion processes", Comp. Science, 30 (2010), pp. 1-13.

Maxime Sermesant, "An Anistropic Multi-front Fast Marching Method for Real-Time Simulation of Cardiac Electrophysiology", FIMH, 2007, pp. 160-169.

Felipe Alonso Atienza, "A Probabilistic Model of Cardiac Electrical Activity Based on a Cellular Automata System", Rev Esp Cardiol., 2005, 58(1), pp. 41-47.

Adityo Prakosa, "Personalized virtual-heart technology for guiding the ablation of infarct-related ventricular tachycardia", Nature Biomedical Engineering, Oct. 2018.

Hermenegild J. Arevalo, "Arrhythmia risk stratification of patients after myocardial infarction using personalized heart models", Nature Communications 7:11437 (2016).

Byounghyun Lim, "In situ procedure for high-efficiency computational modeling of atrial fibrillation reflecting personal anatomy, fiber orientation, fibrosis, and electrophysiology", Scientific Reports, (2020) 10:2417.

* cited by examiner

FORECASTED ELECTROANATOMICAL MAPS FOR ABLATION PLANNING

FIELD OF THE INVENTION

The present invention relates generally to the field of electrophysiology, and particularly to the mapping and treatment of cardiac arrhythmias.

BACKGROUND

The local activation time (LAT) at any portion of cardiac tissue is the difference between (i) the time at which the tissue becomes electrically activated during any cardiac cycle, and (ii) a reference time during the same cycle. The reference time may be set, for example, to a point in the QRS complex of a body-surface electrocardiogram (ECG) or a coronary-sinus electrogram signal.

US Patent Application Publication No. 2020/0146579 to Bar-Tal et al., whose disclosure is incorporated herein by reference, describes a method including receiving an input mesh representation of a cardiac chamber, a set of measured locations on a wall tissue of the cardiac chamber, and a respective set of local activation times (LATs) measured at the locations. The input mesh is re-meshed into a regular mesh including regularized polygons. The set of measured locations and respective LATs is data-fitted to the regularized polygons. Respective LAT values, and respective probabilities that the wall tissue includes scar tissue, are iteratively calculated for the regularized polygons, so as to obtain an electrophysiological (EP) activation wave over the regular mesh that indicates scar tissue. An electroanatomical map overlaid on the regular mesh, the map including the EP activation wave and the scar tissue, is presented.

U.S. Pat. No. 9,463,072 describes a method and system for patient-specific planning and guidance of electrophysiological interventions. A patient-specific anatomical heart model is generated from cardiac image data of a patient. A patient-specific cardiac electrophysiology model is generated based on the patient-specific anatomical heart model and patient-specific electrophysiology measurements. Virtual electrophysiological interventions are performed using the patient-specific cardiac electrophysiology model. A simulated electrocardiogram (ECG) signal is calculated in response to each virtual electrophysiological intervention.

US Patent Application Publication No. 2017/0027649 describes a method for guiding electrophysiology (EP) intervention using a patient-specific electrophysiology model, which includes acquiring a medical image of a patient subject. Sparse EP signals are acquired over an anatomy using the medical image for guidance. The sparse EP signals are interpolated using a patient specific computational electrophysiology model and a three-dimensional model of EP dynamics is generated therefrom. A rendering of the three-dimensional model is displayed. Candidate intervention sites are received, effects on the EP dynamics resulting from intervention at the candidate intervention sites is simulated using the model, and a rendering of the model showing the simulated effects is displayed.

Atienza, Felipe Alonso, et al., "A probabilistic model of cardiac electrical activity based on a cellular automata system," Revista Espanola de Cardiologia (English Edition) 58.1 (2005): 41-47 describes a computer model of cardiac electrical activity able to simulate complex electrophysiological phenomena.

Evseev, Alexey A., "Cellular automata simulation on surface triangulation for diffusion processes," Bulletin of the Novosibirsk Computing Center, Series: Computer Science 30 (2010): 1-13 describes techniques for cellular automata simulations on triangulated grids.

Sahli Costabal, Francisco, et al., "Physics-informed neural networks for cardiac activation mapping," Frontiers in Physics 8 (2020): 42 proposes a physics-informed neural network for cardiac activation mapping that accounts for the underlying wave propagation dynamics, and quantifies the epistemic uncertainty associated with these predictions. The reference further illustrates the potential of this approach using a synthetic benchmark problem and a personalized electrophysiology model of the left atrium.

SUMMARY OF THE INVENTION

There is provided, in accordance with some embodiments of the present invention, a system including a display and a processor. The processor is configured to compute multiple forecasted local activation times (LATs) at different respective locations on cardiac tissue of a subject, by simulating a propagation of a physiological activation potential along the cardiac tissue with a particular portion of the cardiac tissue, which is currently conductive, being non-conductive. The processor is further configured to generate, based on the forecasted LATs, a forecasted electroanatomical map representing a forecasted state of the cardiac tissue following an ablation of the particular portion of the cardiac tissue, and to display the forecasted electroanatomical map on the display.

In some embodiments,
the processor is further configured to:
  prior to computing the forecasted LATs, display a current electroanatomical map representing a current state of the cardiac tissue, and
  receive, from a user, a marking of the particular portion of the cardiac tissue on the current electroanatomical map, and
the processor is configured to simulate the propagation in response to receiving the marking.

In some embodiments, the processor is further configured to compute respective forecasted conduction velocities at the locations based on the forecasted LATs, and the processor is configured to generate the forecasted electroanatomical map based on the forecasted conduction velocities.

In some embodiments,
the processor is configured to simulate the propagation of the activation potential by evolving a cellular automata model, which represents the cardiac tissue, over multiple iterations, and
the processor is configured to compute the forecasted LATs in response to identifying respective ones of the iterations during which cells of the model are first active.

In some embodiments, the processor is further configured to define the cells by partitioning a triangular mesh representing the cardiac tissue.

In some embodiments, the cells have respective conduction velocities, and the processor is configured to evolve the model by, during each one of the iterations, for at least one first cell of those of the cells that are inactive:
  identifying at least one second cell of the cells as an activator for the first cell, in response to (i) the conduction velocity of the second cell, (ii) a distance of the second cell from the first cell, and (iii) a number of the iterations that passed since the second cell was last active, and
  in response to identifying the second cell, activating the first cell.

In some embodiments, the processor is further configured to:
prior to computing the forecasted LATs, display a current electroanatomical map representing a current state of the cardiac tissue,
receive, from a user, an indication of a map-portion of the current electroanatomical map, and
initialize the model such that one or more of the cells corresponding to the map-portion of the current electroanatomical map are active, and all others of the cells are inactive.

In some embodiments, the processor is configured to evolve the model by, during each one of the iterations, inactivating any one of the cells that was active for a predefined number of the iterations.

In some embodiments, the predefined number is a first predefined number, and the processor is configured to evolve the model by, during each one of the iterations, refraining from activating any one of the cells that was last active within a second predefined number of the iterations.

There is further provided, in accordance with some embodiments of the present invention, a method, including computing multiple forecasted local activation times (LATs) at different respective locations on cardiac tissue of a subject, by simulating a propagation of a physiological activation potential along the cardiac tissue with a particular portion of the cardiac tissue, which is currently conductive, being non-conductive. The method further comprises, based on the forecasted LATs, generating a forecasted electroanatomical map representing a forecasted state of the cardiac tissue following an ablation of the particular portion of the cardiac tissue, and displaying the forecasted electroanatomical map.

There is further provided, in accordance with some embodiments of the present invention, a computer software product including a tangible non-transitory computer-readable medium in which program instructions are stored. The instructions, when read by a processor, cause the processor to compute multiple forecasted local activation times (LATs) at different respective locations on cardiac tissue of a subject, by simulating a propagation of a physiological activation potential along the cardiac tissue with a particular portion of the cardiac tissue, which is currently conductive, being non-conductive. The instructions further cause the processor to generate, based on the forecasted LATs, a forecasted electroanatomical map representing a forecasted state of the cardiac tissue following an ablation of the particular portion of the cardiac tissue, and to display the forecasted electroanatomical map on the display.

BRIEF DESCRIPTION OF THE DRAWINGS

The present invention will be more fully understood from the following detailed description of embodiments thereof, taken together with the drawings, in which.

DETAILED DESCRIPTION OF EMBODIMENTS

Overview

Embodiments of the present invention facilitate the planning of an ablation of cardiac tissue of a subject by forecasting the LATs that will result from the ablation.

First, the physician is shown an electroanatomical map of the tissue. The physician marks, on the map, the portion of the tissue that is planned for ablation. Typically, the physician also indicates, with reference to the map, the anatomical location from which an activation wave originates during each cardiac cycle.

Subsequently, based on the aforementioned input from the physician, a computer processor simulates the propagation of the activation wave along the cardiac tissue following the planned ablation. Based on the simulation, the processor computes the forecasted LATs. Finally, the processor displays a forecasted electroanatomical map that is colored and/or otherwise annotated so as to indicate the forecasted LATs. Based on the forecasted map, the physician may ascertain whether the planned ablation will be effective. For example, if the subject suffers from a stable tachycardia, the physician may ascertain whether the planned ablation will interrupt the circuit that generates the tachycardia.

In some embodiments, the processor simulates the propagation of the activation wave by evolving a cellular automata model, which represents the cardiac tissue, over multiple iterations. For each cellular automaton (hereinafter "cell") of the model that is active at least once during the simulation, the processor identifies the iteration during which the cell was first active, and computes the forecasted LAT for the cell based on the number of the identified iteration. Thus, for example, a cell activated during an earlier iteration will have a lower forecasted LAT than another cell activated during a later iteration.

Typically, the processor evolves the model based on the respective conduction velocities of the cells, which are derived from the original electroanatomical map. Thus, for example, a cell may be activated by a neighboring cell that was active during the immediately-preceding iteration, provided that the neighboring cell has a sufficiently large conduction velocity. On the other hand, if the neighboring cell has a smaller conduction velocity, the cell may be activated by the neighboring cell only if the neighboring cell was active during an earlier iteration.

Typically, the processor also computes forecasted conduction velocities based on the forecasted LATs, and the forecasted electroanatomical map is annotated so as to indicate the forecasted conduction velocities.

System Description

Figure 1:
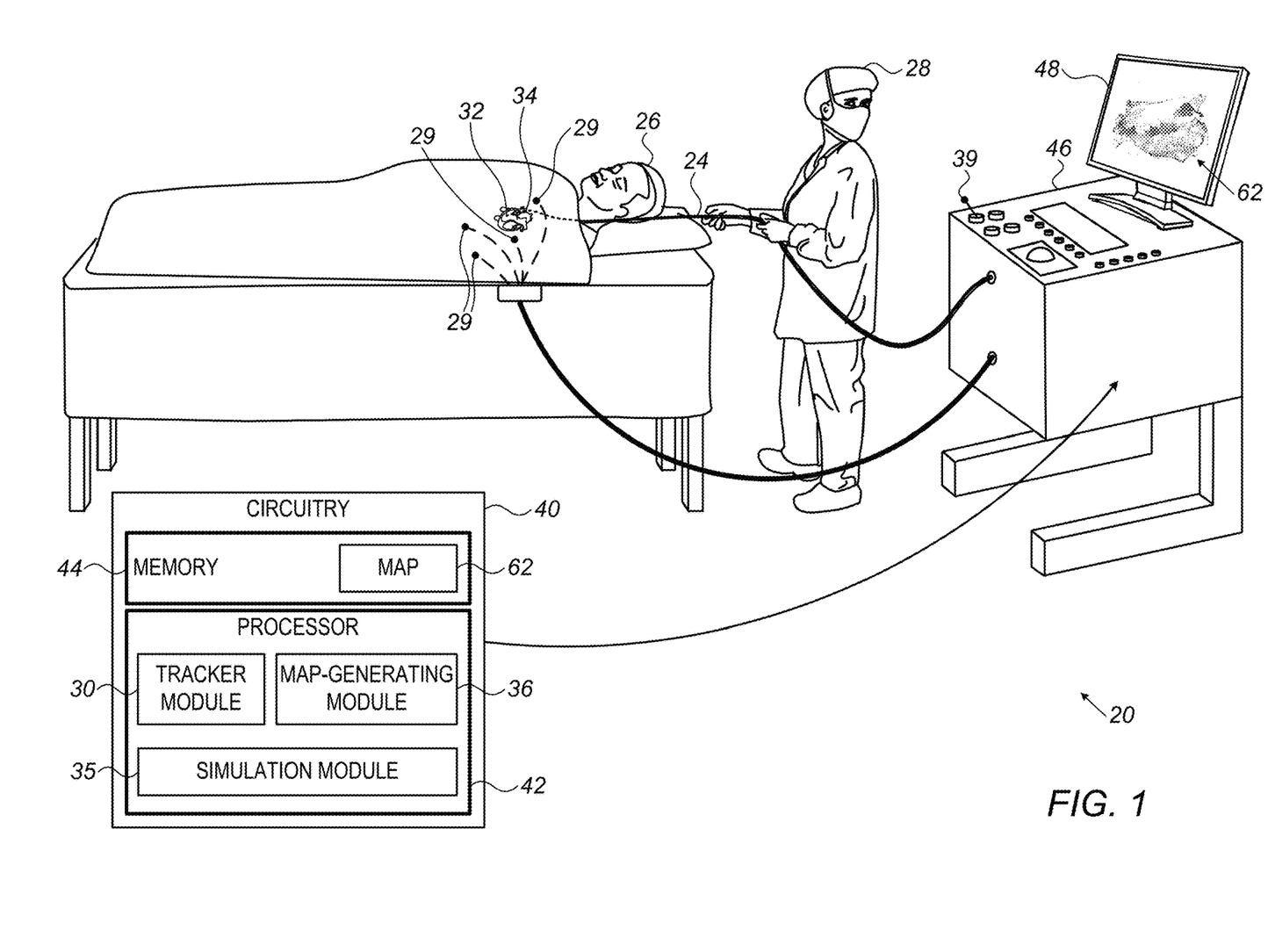
FIG. 1 is a schematic illustration of a system for planning an ablation of cardiac tissue, in accordance with some exemplary embodiments of the present invention.

Reference is initially made to FIG. 1, which is a schematic illustration of a system 20 for planning an ablation of cardiac tissue, in accordance with some embodiments of the present invention.

System 20 comprises a probe 24, configured for insertion into the body of a subject 26 by a physician 28. System 20 further comprises a console 46, comprising user-interface controls 39 for facilitating interaction of physician 28 with system 20.

System 20 further comprises circuitry 40, which is typically contained within console 46. Circuitry 40 comprises a processor 42 and a memory 44, which may comprise any suitable volatile memory and/or non-volatile memory. Typically, circuitry 40 further comprises a noise-removal filter and an analog-to-digital (A/D) converter.

The distal end of probe 24 comprises one or more electrodes 32. Subsequently to inserting probe 24 into the body of subject 26, physician 28 navigates the probe to the heart 34 of the subject. Subsequently, physician 28 uses electrodes 32 to measure electrogram signals from tissue of heart 34. Processor 42 receives the electrogram signals, typically via the aforementioned noise-removal filter and A/D converter.

System 20 further comprises a tracking subsystem, which, for ease of illustration, is omitted from FIG. 1. The tracking subsystem is configured to facilitate tracking the respective locations of electrodes 32 within heart 34, such that processor 42 may associate each received electrogram signal with the location on the cardiac tissue at which the signal was acquired. In some embodiments, processor 42 tracks the electrode locations by executing a tracker module 30, which interacts with the tracking subsystem.

In some embodiments, the tracking subsystem comprises one or more electromagnetic sensors at the distal end of probe 24, along with one or more magnetic-field generators configured to generate a magnetic field. The magnetic field induces tracking signals in the electromagnetic sensors. Based on the tracking signals, processor 42 (e.g., tracker module 30) ascertains the locations of the sensors, and hence, of the electrodes. Such location-tracking techniques are disclosed, for example, in U.S. Pat. Nos. 5,391,199, 5,443,489, and 6,788,967 to Ben-Haim, in U.S. Pat. No. 6,690,963 to Ben-Haim et al., in U.S. Pat. No. 5,558,091 to Acker et al., and in U.S. Pat. No. 6,177,792 to Govari, whose respective disclosures are incorporated herein by reference.

Alternatively or additionally, the tracking subsystem may comprise one or more reference electrodes electrically coupled to the body of the subject. Electric currents may be passed between electrodes 32 and the reference electrodes. Based on the resulting current or voltage distribution, processor 42 (e.g., tracker module 30) may ascertain the locations of electrodes 32. Such techniques may utilize a location map calibrated, in advance, using electromagnetic sensors, as described, for example, in U.S. Pat. No. 7,536,218 to Govari et al. and U.S. Pat. No. 8,456,182 to Bar-Tal et al., whose respective disclosures are incorporated herein by reference.

Alternatively or additionally, electric currents may be passed between the reference electrodes. Based on the resulting voltages at electrodes 32, processor 42 (e.g., tracker module 30) may ascertain the locations of electrodes 32, as described, for example, in U.S. Pat. No. 5,983,126 to Wittkampf and U.S. Pat. No. 5,944,022 to Nardella, whose respective disclosures are incorporated herein by reference.

System 20 further comprises one or more ECG electrodes 29, which are electrically coupled to the skin of subject 26. Processor 42 receives the ECG signals acquired by electrodes 29, typically via the aforementioned noise-removal filter and A/D converter.

Based on the electrogram and ECG signals, processor 42 generates an electroanatomical map 62, which combines a representation of the anatomy of the tissue with electrical properties of the tissue. For example, a three-dimensional triangular mesh representing the tissue may be colored in accordance with a color scale so as to indicate, for each element of the mesh, an LAT that was computed for the portion of tissue represented by the element. Alternatively or additionally, vectors representing conduction velocities may be overlaid on the mesh.

In some embodiments, the processor generates map 62 by executing a map-generating module 36. In generating map 62, processor 42 accounts for the "reentries" observed in cyclic arrhythmias, as described in US Patent Application Publication No. 2020/0146579 to Bar-Tal et al., whose disclosure is incorporated herein by reference.

Subsequently to generating map 62, processor 42 displays the map on a display 48 and, typically, stores the map in memory 44. Subsequently, physician 28 (or another user) provides input relating to a planned ablation of the tissue. The input may be provided, for example, using a touch screen belonging to display 48 or using any suitable user-interface control 39, such as a mouse or trackball. The input may include, for example, a marking of the portion of the tissue that the physician plans to ablate.

Subsequently, based on the input, the processor computes multiple forecasted LATs at different respective locations on the tissue, by simulating a propagation of a physiological activation potential (or "activation wave") along the tissue following the planned ablation. In other words, the processor simulates the propagation with the particular portion of tissue that the physician plans to ablate, which is currently conductive, being non-conductive. In some embodiments, the processor performs the simulation by executing a simulation module 35.

Subsequently, based on the forecasted LATs, the processor (e.g., map-generating module 36) generates a forecasted electroanatomical map representing the forecasted state of the tissue following the ablation. The forecasted electroanatomical map is then displayed on display 48 and, typically, stored in memory 44. Based on the forecasted map, the physician may decide whether to proceed with the planned ablation.

Typically, system 20 further comprises an ablation-signal generator (not shown). Subsequently to deciding to proceed with the planned ablation, physician 28 may control the ablation-signal generator, using user-interface controls 39, so as to deliver ablating signals to electrodes 32.

In general, processor 42 may be embodied as a single processor, or as a cooperatively networked or clustered set of processors. The functionality of processor 42 may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, processor 42 may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Computing Forecasted Electroanatomical Maps

Figure 2:
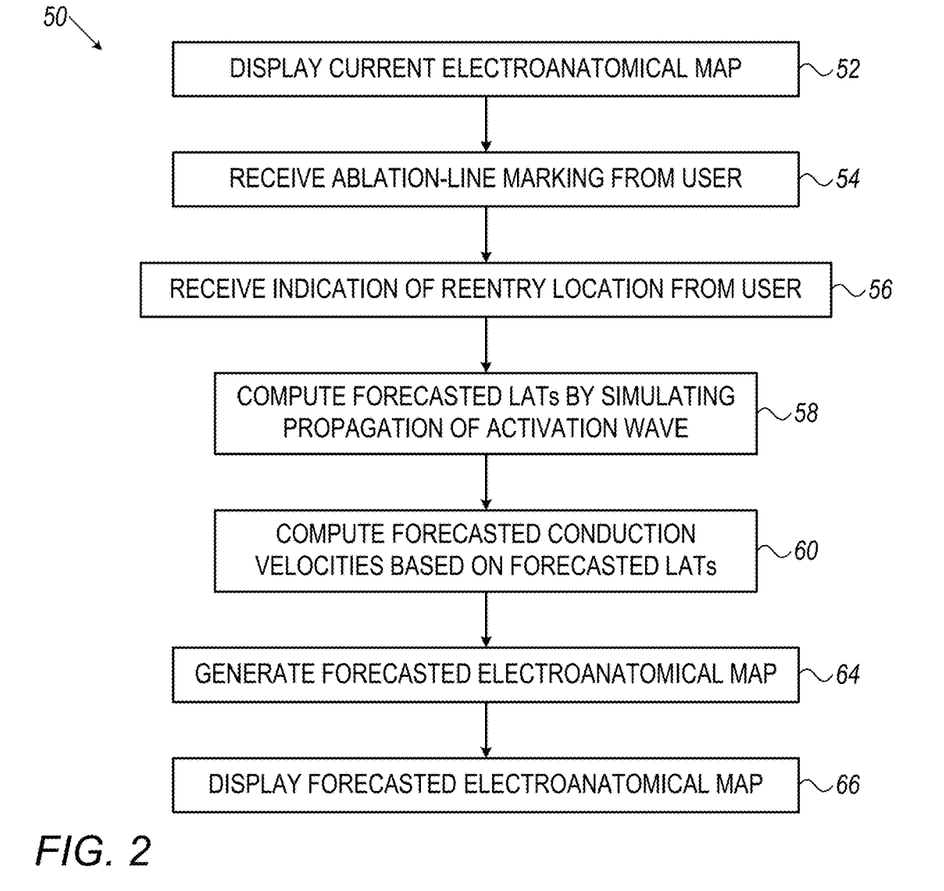
FIG. 2 is a flow diagram for an algorithm for generating and displaying a forecasted electroanatomical map, in accordance with some exemplary embodiments of the present invention.

Reference is now made to FIG. 2, which is a flow diagram for an algorithm 50 for generating and displaying a forecasted electroanatomical map, in accordance with some embodiments of the present invention. Algorithm 50 may be executed by processor 42 (FIG. 1).

Typically, algorithm 50 begins with a first displaying step 52, at which the processor displays electroanatomical map 62 (FIG. 1), which represents the current (pre-ablation) state of the cardiac tissue.

Typically, while map 62 is displayed, the physician marks, on the map, the portion of tissue planned for ablation, this marking typically having the form of a line referred to herein as an "ablation line." This marking is received by the processor at a marking-receiving step 54. Alternatively or additionally, the physician may indicate the portion of the map representing the anatomical location from which the activation wave originates, such as a reentry location. For example, the physician may click a mouse on the portion of the map. This indication is received by the processor at an indication-receiving step 56.

Next, at a simulating step 58, the processor computes forecasted LATs at different respective locations on the tissue, by simulating a propagation of an activation wave along the tissue.

In some embodiments, as further described below with reference to FIGS. 3-4, the processor simulates the propagation by evolving a cellular automata model, which represents the cardiac tissue, over multiple iterations. Each cell in the model may either be active (i.e., "on"), which simulates the anatomical state of depolarization, or inactive (i.e., "off"), which simulates the polarized (or "resting") state. For each cell that is active at any point during the simulation, the processor identifies the iteration during which the cell was first active, and computes the forecasted LAT for the cell in response thereto.

In other embodiments, the processor simulates the propagation by solving a system of diffusion equations, e.g., using finite elements. Alternatively, the processor may use the Fast Marching method, e.g., as described in Sermesant, Maxime, et al., "An anisotropic multi-front fast marching method for real-time simulation of cardiac electrophysiology," International Conference on Functional Imaging and Modeling of the Heart, Springer, Berlin, Heidelberg, 2007, whose disclosure is incorporated herein by reference. As yet another option, the processor may use a neural network simulator as described, for example, in Sahli Costabal, Francisco, et al., "Physics-informed neural networks for cardiac activation mapping," Frontiers in Physics 8 (2020): 42, whose disclosure is incorporated herein by reference.

Typically, the processor then performs a computing step 60, at which the processor computes respective forecasted conduction velocities at the locations based on the forecasted LATs.

Subsequently, at a generating step 64, the processor generates a forecasted electroanatomical map based on the forecasted LATs and, optionally, the forecasted conduction velocities. For example, the processor may color the forecasted electroanatomical map so as to indicate the forecasted LATs, and/or overlay vectors representing the conduction velocities, as described for map 62 with reference to FIG. 1. Finally, at a second displaying step 66, the processor displays the forecasted map.

Figure 3:
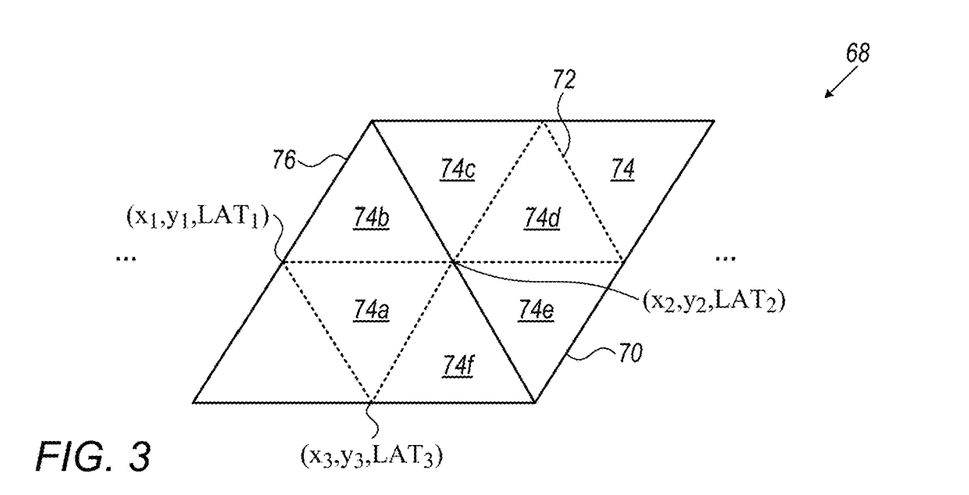
FIG. 3 is a schematic illustration of a portion of a partitioned triangular mesh, in accordance with some exemplary embodiments of the present invention.
Figure 4:
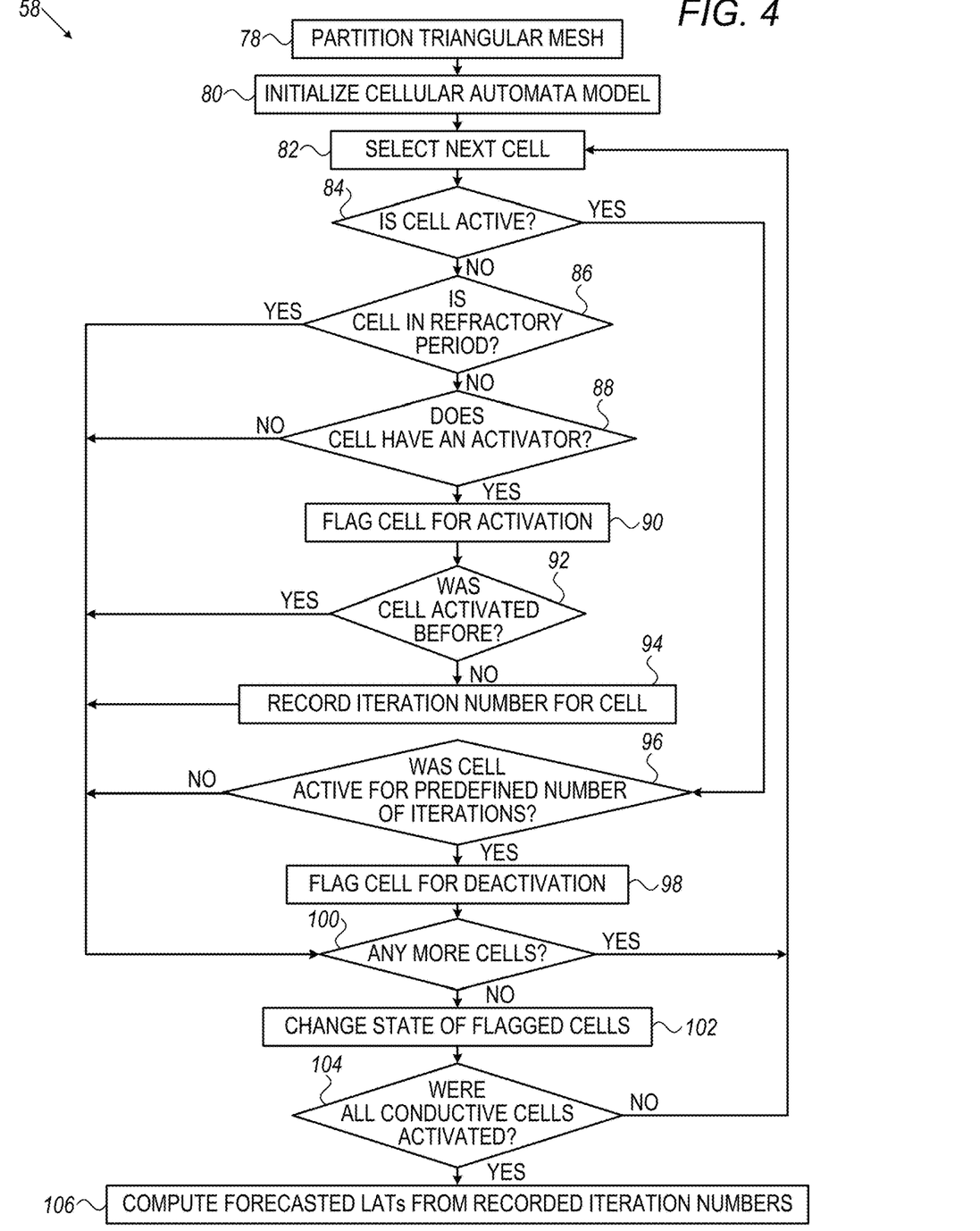
FIG. 4 is a flow diagram for an embodiment of a simulating step in which a cellular automata model is evolved, in accordance with some exemplary embodiments of the present invention.

Reference is now made to FIG. 3, which is a schematic illustration of a portion of a partitioned triangular mesh 68, in accordance with some embodiments of the present invention. Reference is further made to FIG. 4, which is a flow diagram for an embodiment of simulating step 58 of algorithm 50 (FIG. 2) in which a cellular automata model is evolved, in accordance with some embodiments of the present invention.

Mesh 68, which belongs to map 62 (FIG. 1), represents the cardiac tissue. A solid border 70 in FIG. 3 delineates two triangles 76 in mesh 68.

To increase the accuracy of the forecasted LATs, it may be advantageous for cells 74 of the cellular automata model to be smaller than triangles 76. Hence, in some embodiments, simulating step 58 begins with a partitioning step 78, at which the processor defines cells 74 by partitioning mesh 68. For example, as indicated by dashed lines 72 in FIG. 3, the processor may partition each triangle 76 into four triangular cells 74. It is noted that the sizes of triangles 76 may differ from each other, and hence, the sizes of cells 74 may also differ from each other.

At an initializing step 80, the processor initializes the model by setting one or more cells 74 to the active state, and all the remaining cells to the inactive state. The cells set to active are those corresponding to the portion of map 62 representing the anatomical location from which the activation wave originates, which, as described above with reference to FIG. 2, may be indicated by the physician.

Following the initialization, the processor iteratively evolves the model. During each iteration, each cell 74 that is conductive (i.e., that represents conductive tissue) is selected at a selecting step 82. Subsequently to selecting the cell, the processor checks, at a checking step 84, whether the cell is active. If not, the processor checks, at another checking step 86, whether the cell is in a refractory period, i.e., whether the cell was previously active within a predefined number of iterations. If yes, the processor refrains from activating the cell, and instead proceeds to another checking step 100, described below. Otherwise, the processor checks, at another checking step 88, whether the cell has at least one activator, as further described below. If not, the processor proceeds to checking step 100. Otherwise, the cell is flagged for activation at a flagging step 90.

Subsequently to performing flagging step 90, the processor checks, at another checking step 92, whether the cell was activated before. If not, the processor, at a recording step 94, records the current iteration number for the cell. Subsequently, or if the cell was activated before, the processor proceeds to checking step 100.

On the other hand, if, at checking step 84, the processor ascertains that the cell is active, the processor checks, at another checking step 96, whether the cell was active for a predefined number of iterations. If yes, the cell is flagged for deactivation at another flagging step 98. Subsequently, or if the cell was not active for the predefined number of iterations, the processor performs checking step 100.

At checking step 100, the processor checks whether any more cells remain to be selected during the current iteration. If yes, the processor returns to selecting step 82 and selects the next cell. Otherwise, the processor, at an evolving step 102, evolves the model by changing the state of the flagged cells. In other words, the processor activates the cells flagged for activation and deactivates the cells flagged for deactivation. Subsequently, the processor checks, at another checking step 104, whether all of the conductive cells were activated during the simulation. If not, the processor returns to selecting step 82, and performs another iteration of the evolution.

Upon ascertaining, at checking step 104, that all of the conductive cells were activated, the processor, at a computing step 106, computes forecasted LATs from the recorded iteration numbers. For example, given a recorded iteration number n (where n=1 indicates the first iteration), the processor may compute the forecasted LAT as n*T/N, where T is the cycle length (as calculated during the generation of the current electroanatomical map) and N is the total number of performed iterations.

Typically, the cells have respective conduction velocities, which are based on the conduction velocities computed during the generation of the current electroanatomical map. For example, each cell may have the conduction velocity of the triangle 76 from which the cell was partitioned. (Cells representing nonconductive tissue may be assigned a conduction velocity of zero.) The processor uses the conduction velocities when performing checking step 88. For example, the processor may identify another cell as an activator for the selected cell in response to (i) the conduction velocity of the other cell, (ii) the distance of the other cell from the selected cell, and (iii) the number of iterations that passed since the other cell was last active.

For example, supposing the $i^{th}$ cell is selected, the processor may first identify the set of cells that neighbor the $i^{th}$ cell, i.e., that share at least one edge with the $i^{th}$ cell. The processor may then iterate through the set, checking each cell in the set until an activator is found or the set is exhausted. In particular, for each $j^{th}$ cell that is checked, the processor may perform the following sequence of steps:

(a) Compute $r_j$, an estimated distance travelled by an activation wave across the $j^{th}$ cell during a single iteration, as a function of $\vec{v}_j$, the conduction velocity of the $j^{th}$ cell. In some embodiments, $r_j = a - b/\|\vec{v}_j\|$ where a and b are suitable constants. In some such embodiments, the constant a is set responsively to the average or median distance between all pairs of neighboring cells. (Typically, the distance between two cells is defined as the distance between the respective centroids of the cells.)
  (b) Compute $n = \text{ceil}(d_{ij}/r_j)$, where $d_{ij}$ is the distance between the $i^{th}$ cell and the $j^{th}$ cell, and the ceil( ) function rounds the argument up to the nearest integer.
  (c) If the $j^{th}$ cell was active n iterations ago, identify the $j^{th}$ cell as an activator for the $i^{th}$ cell. Otherwise, check the next neighboring cell in the set.

As noted above with reference to computing step 60 of algorithm 50 (FIG. 2), the processor typically computes forecasted conduction velocities based on the forecasted LATs. For example, the processor may calculate a forecasted conduction velocity $\vec{u}_i$ for the $i^{th}$ cell as follows:

(a) Compute respective forecasted vertex-LATs {$LAT_1$, $LAT_2$, $LAT_3$} for the vertices of the cell, each of the vertex-LATs typically being an average of the forecasted LATs of the cells that share the vertex. For example, $LAT_2$ for cell 74a, as shown in FIG. 3, may be the average of the respective forecasted LATs of cells 74a ... 74f.
  (b) Compute the coordinates {$(x_1,y_1)$, $(x_2,y_2)$, $(x_3,y_3)$} of the vertices following a projection of the cell from the three-dimensional coordinate system of the mesh to two dimensions.
  (c) Solve the following system of equations for the inverse-speed (or "slowness") variables $s_x$ and $s_y$:

$$LAT_3 - LAT_1 = (s_x, s_y) \cdot (x_3 - x_1, y_3 - y_1) \quad \text{(i)}$$

$$LAT_2 - LAT_1 = (s_x, s_y) \cdot (x_2 - x_1, y_2 - y_1) \quad \text{(ii)}$$

(d) Solve the equation $\vec{s}_i = \vec{w}_i / \vec{w}_i \vec{w}_i$ for $\vec{w}_i$, where $\vec{s}_i = (s_x, s_y)$.
  (e) Compute $\vec{u}_i$ as the projection of $\vec{w}_i$ to the coordinate system of the mesh, by applying the inverse of the transformation applied in step (b).

Example Forecasted Electroanatomical Map

Figure 5:
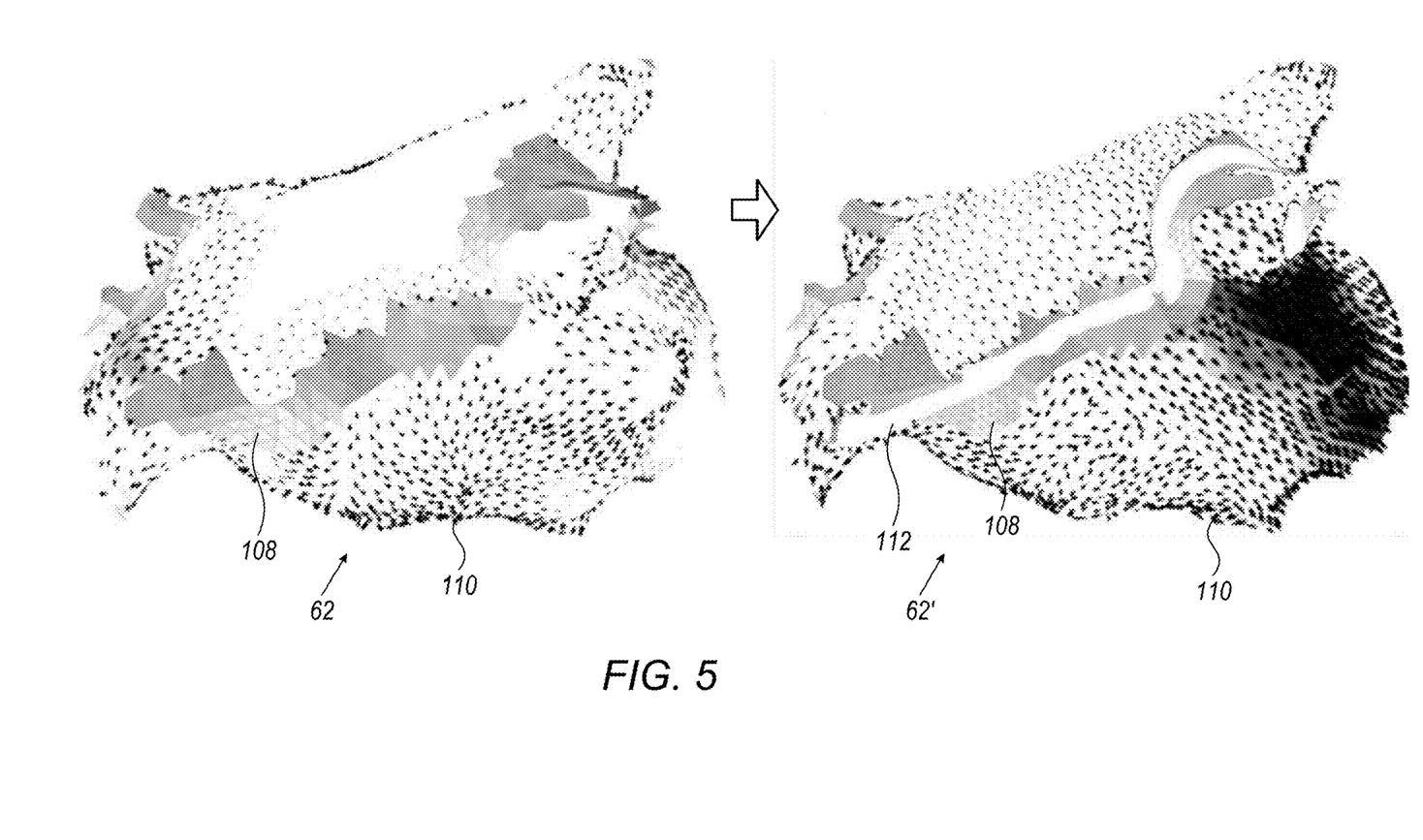
FIG. 5 is a schematic illustration of an example electroanatomical map and a corresponding forecasted electroanatomical map, in accordance with some exemplary embodiments of the present invention.

Reference is now made to FIG. 5, which is a schematic illustration of an example electroanatomical map 62 and a corresponding forecasted electroanatomical map 62', in accordance with some embodiments of the present invention.

Typically, map 62 is colored per a color scale so as to indicate the computed LATs, as described above with reference to FIG. 1. In such embodiments, a particular color that does not belong to the color scale may indicate slow-conducting (including non-conducting) tissue. To illustrate this, FIG. 5 "colors" map 62 using multiple brightness levels, with shades of gray in a region 108 of the map indicating slow-conducting tissue. Outside of region 108, vectors 110 indicate conduction velocities.

In response to viewing map 62, the physician may mark an ablation line 112 passing through region 108. The physician may further indicate a reentry location. Subsequently, the processor may compute forecasted LATs and conduction velocities, as described above with reference to the previous figures. Based on these forecasted values, the processor may generate and display forecasted map 62'.

In some embodiments, the forecasted map includes the finer mesh computed at partitioning step 78 (FIG. 4), as shown in FIG. 5. In other embodiments, the forecasted map includes the original triangular mesh of map 62, the forecasted LATs and conduction velocities being projected onto this mesh.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for ablation planning, the system comprising:
a display; and
a processor, configured to:
  compute multiple forecasted local activation times (LATs) at different respective locations on cardiac tissue of a subject, by simulating a propagation of a physiological activation potential along the cardiac tissue with a particular portion of the cardiac tissue, which is currently conductive, being non-conductive,
  based on the forecasted LATs, generate a forecasted electroanatomical map representing a forecasted state of the cardiac tissue following an ablation of the particular portion of the cardiac tissue,
  display the forecasted electroanatomical map on the display, simulate the propagation of the activation potential by evolving a cellular automata model, which represents the cardiac tissue, over multiple iterations, compute the forecasted LATs in response to identifying respective ones of the iterations during which cells of the cellular automata model are first active, prior to computing the forecasted LATs, display a current electroanatomical map representing a current state of the cardiac tissue, receive, from a user, an indication of a map-portion of the current electroanatomical map, and initialize the cellular automata model such that one or more of the cells corresponding to the map-portion of the current electroanatomical map are active, and all others of the cells are inactive.

2. The system according to claim 1,
wherein the processor is configured to simulate the propagation in response to receiving the marking.

3. The system according to claim 1, wherein the processor is further configured to compute respective forecasted conduction velocities at the locations based on the forecasted LATs, and wherein the processor is configured to generate the forecasted electroanatomical map based on the forecasted conduction velocities.

4. The system according to claim 1, wherein the processor is further configured to define the cells by partitioning a triangular mesh representing the cardiac tissue.

5. The system according to claim 1, wherein the cells have respective conduction velocities, and wherein the processor is configured to evolve the model by, during each one of the iterations, for at least one first cell of those of the cells that are inactive:
identifying at least one second cell of the cells as an activator for the first cell, in response to (i) the conduction velocity of the second cell, (ii) a distance of the second cell from the first cell, and (iii) a number of the iterations that passed since the second cell was last active, and in response to identifying the second cell, activating the first cell.

6. The system according to claim 1, wherein the processor is configured to evolve the model by, during each one of the iterations, inactivating any one of the cells that was active for a predefined number of the iterations.

7. The system according to claim 6, wherein the predefined number is a first predefined number, and wherein the processor is configured to evolve the model by, during each one of the iterations, refraining from activating any one of the cells that was last active within a second predefined number of the iterations.

8. A method for ablation planning, the method comprising:
computing multiple forecasted local activation times (LATs) at different respective locations on cardiac tissue of a subject, by simulating a propagation of a physiological activation potential along the cardiac tissue with a particular portion of the cardiac tissue, which is currently conductive, being non-conductive;

based on the forecasted LATs, generating a forecasted electroanatomical map representing a forecasted state of the cardiac tissue following an ablation of the particular portion of the cardiac tissue; and displaying the forecasted electroanatomical map,
wherein simulating the propagation of the activation potential comprises simulating the propagation of the activation potential by evolving a cellular automata model, which represents the cardiac tissue, over multiple iterations, and wherein computing the forecasted LATs comprises computing the forecasted LATs in response to identifying respective ones of the iterations during which cells of the cellular automata model are first active.

9. The method according to claim 8, further comprising:
prior to computing the forecasted LATs, displaying a current electroanatomical map representing a current state of the cardiac tissue; and receiving, from a user, a marking of the particular portion of the cardiac tissue on the current electroanatomical map, wherein simulating the propagation comprises simulating the propagation in response to receiving the marking.

10. The method according to claim 8, further comprising computing respective forecasted conduction velocities at the locations based on the forecasted LATs, wherein generating the forecasted electroanatomical map comprises generating the forecasted electroanatomical map based on the forecasted conduction velocities.

11. The method according to claim 8, further comprising defining the cells by partitioning a triangular mesh representing the cardiac tissue.

12. The method according to claim 8, wherein the cells have respective conduction velocities, and wherein evolving the model comprises, during each one of the iterations, for at least one first cell of those of the cells that are inactive:
identifying at least one second cell of the cells as an activator for the first cell, in response to (i) the conduction velocity of the second cell, (ii) a distance of the second cell from the first cell, and (iii) a number of the iterations that passed since the second cell was last active, and in response to identifying the second cell, activating the first cell.

13. The method according to claim 8, further comprising:
prior to computing the forecasted LATs, displaying a current electroanatomical map representing a current state of the cardiac tissue;

receiving, from a user, an indication of a map-portion of the current electroanatomical map; and initializing the model such that one or more of the cells corresponding to the map-portion of the current electroanatomical map are active, and all others of the cells are inactive.

14. The method according to claim 8, wherein evolving the model comprises, during each one of the iterations, inactivating any one of the cells that was active for a predefined number of the iterations.

15. The method according to claim 14, wherein the predefined number is a first predefined number, and wherein evolving the model further comprises, during each one of the iterations, refraining from activating any one of the cells that was last active within a second predefined number of the iterations.

16. A computer software product comprising a tangible non-transitory computer-readable medium in which program instructions are stored, which instructions, when read by a processor, cause the processor to:
compute multiple forecasted local activation times (LATs) at different respective locations on cardiac tissue of a subject, by simulating a propagation of a physiological activation potential along the cardiac tissue with a particular portion of the cardiac tissue, which is currently conductive, being non-conductive, based on the forecasted LATs, generate a forecasted electroanatomical map representing a forecasted state of the cardiac tissue following an ablation of the particular portion of the cardiac tissue, and display the forecasted electroanatomical map on a display, the display being coupled with the processor, wherein the instructions cause the processor to simulate the propagation of the activation potential by evolving a cellular automata model, which represents the cardiac tissue, over multiple iterations, and wherein the instructions cause the processor to compute the forecasted LATs in response to identifying respective ones of the iterations during which cells of the model are first active.

* * * * *